(12) United States Patent
Bakhshandeh

(10) Patent No.: US 7,798,961 B1
(45) Date of Patent: Sep. 21, 2010

(54) ACQUISITION AND MANAGEMENT OF TIME DEPENDENT HEALTH INFORMATION

(75) Inventor: Shahin Bakhshandeh, San Francisco, CA (US)

(73) Assignee: BeWell Mobile Technology Inc., San Francisco, CA (US)

( * ) Notice: Subject to any disclaimer, the term of this patent is extended or adjusted under 35 U.S.C. 154(b) by 0 days.

(21) Appl. No.: 11/073,408

(22) Filed: Mar. 4, 2005

Related U.S. Application Data

(60) Provisional application No. 60/643,375, filed on Jan. 11, 2005.

(51) Int. Cl.
*A61B 5/00* (2006.01)
(52) U.S. Cl. .......................... 600/300; 705/2
(58) Field of Classification Search ................ 600/300, 600/301; 128/903–905, 920; 705/2–4
See application file for complete search history.

(56) References Cited

U.S. PATENT DOCUMENTS

| | | | |
|---|---|---|---|
| 5,840,020 A | 11/1998 | Heinonen et al. | |
| 6,024,699 A * | 2/2000 | Surwit et al. | 600/300 |
| 6,168,563 B1 | 1/2001 | Brown | |
| 6,231,519 B1 * | 5/2001 | Blants et al. | 600/529 |
| 6,421,633 B1 | 7/2002 | Heinonen et al. | |
| 6,440,068 B1 * | 8/2002 | Brown et al. | 600/300 |
| 6,478,736 B1 * | 11/2002 | Mault | 600/300 |
| 6,485,416 B1 | 11/2002 | Platt et al. | |
| 6,602,191 B2 * | 8/2003 | Quy | 600/300 |
| 6,656,114 B1 * | 12/2003 | Poulsen et al. | 600/300 |
| 6,699,188 B2 * | 3/2004 | Wessel | 600/300 |
| 6,975,963 B2 * | 12/2005 | Hamilton et al. | 702/182 |
| 2002/0198473 A1 | 12/2002 | Kumar et al. | |
| 2003/0050537 A1 | 3/2003 | Wessel | |
| 2003/0086338 A1 | 5/2003 | Sastry et al. | |
| 2003/0208113 A1 * | 11/2003 | Mault et al. | 600/316 |
| 2003/0212317 A1 | 11/2003 | Kovatchev et al. | |
| 2003/0233257 A1 | 12/2003 | Matian et al. | |
| 2004/0059599 A1 | 3/2004 | McIvor | |

* cited by examiner

*Primary Examiner*—Henry M Johnson, III
*Assistant Examiner*—Kai Rajan
(74) *Attorney, Agent, or Firm*—Van Pelt, Yi & James LLP

(57) ABSTRACT

A method for acquiring and managing time dependent health information is disclosed. The method comprises inputting the time dependent health information to a mobile device, time stamping the time dependent health information, and storing the time stamped time dependent health information. The method further comprises detecting the availability of a connection to a server and uploading the time stamped time dependent health information and a user identifier to the server.

26 Claims, 17 Drawing Sheets

ACQUISITION AND MANAGEMENT OF TIME DEPENDENT HEALTH INFORMATION

CROSS REFERENCE TO OTHER APPLICATIONS

This application claims priority to U.S. Provisional Patent Application No. 60/643,375 entitled DIABETES ASSISTANT filed Jan. 11, 2005 which is incorporated herein by reference for all purposes.

FIELD OF THE INVENTION

The present invention relates generally to health information. More specifically, acquisition and management of time dependent health information is disclosed.

BACKGROUND OF THE INVENTION

Patients diagnosed with chronic illness often must make doctor-recommended lifestyle changes. They need to adopt a new self-management regimen encompassing, among other things, diet, exercise, medication, testing, monitoring, and regularly scheduled visits with their health care practice team that includes doctors (including specialists), clinical nurses (including specialists), pharmacists, health educators, and nutritionists who often lack information about how patients are doing between appointment visits. People who are able to follow these recommended lifestyle changes, comply with their self-management regimen, and communicate more effectively with their health care practice team are likely to have better individual health outcomes. Better health outcomes for chronically ill patients result in more efficient use of health care resources spent on chronic disease. One problem is that it is difficult to adopt and maintain the new self-management regimen. One effective tool in enabling compliance to the new self-management regimen is to have effective and timely communication and information-sharing between patients and their support team. This communication between patients and support team is critical for and inherent to the success in chronically ill patients sticking to their new regimens. It would be useful if there were a way to have an interactive way for the patient to have tools to help self-monitor adherence to the new regimen as well as to help others monitor adherence to the new regimen.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process, an apparatus, a system, a composition of matter, a computer readable medium such as a computer readable storage medium or a computer network wherein program instructions are sent over optical or electronic communication links. In this specification, these implementations, or any other form that the invention may take, may be referred to as techniques. A component such as a processor or a memory described as being configured to perform a task includes both a general component that is temporarily configured to perform the task at a given time or a specific component that is manufactured to perform the task. In general, the order of the steps of disclosed processes may be altered within the scope of the invention.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Acquiring and managing time dependent health information is disclosed. Acquiring and managing time dependent health information comprises inputting the time dependent health information to a mobile device, time stamping the time dependent health information, and storing the time stamped time dependent health information. Acquiring and managing time dependent health information further comprises detecting the availability of a connection to a server and uploading the time stamped time dependent health information and a user identifier to the server.

Figure 1:
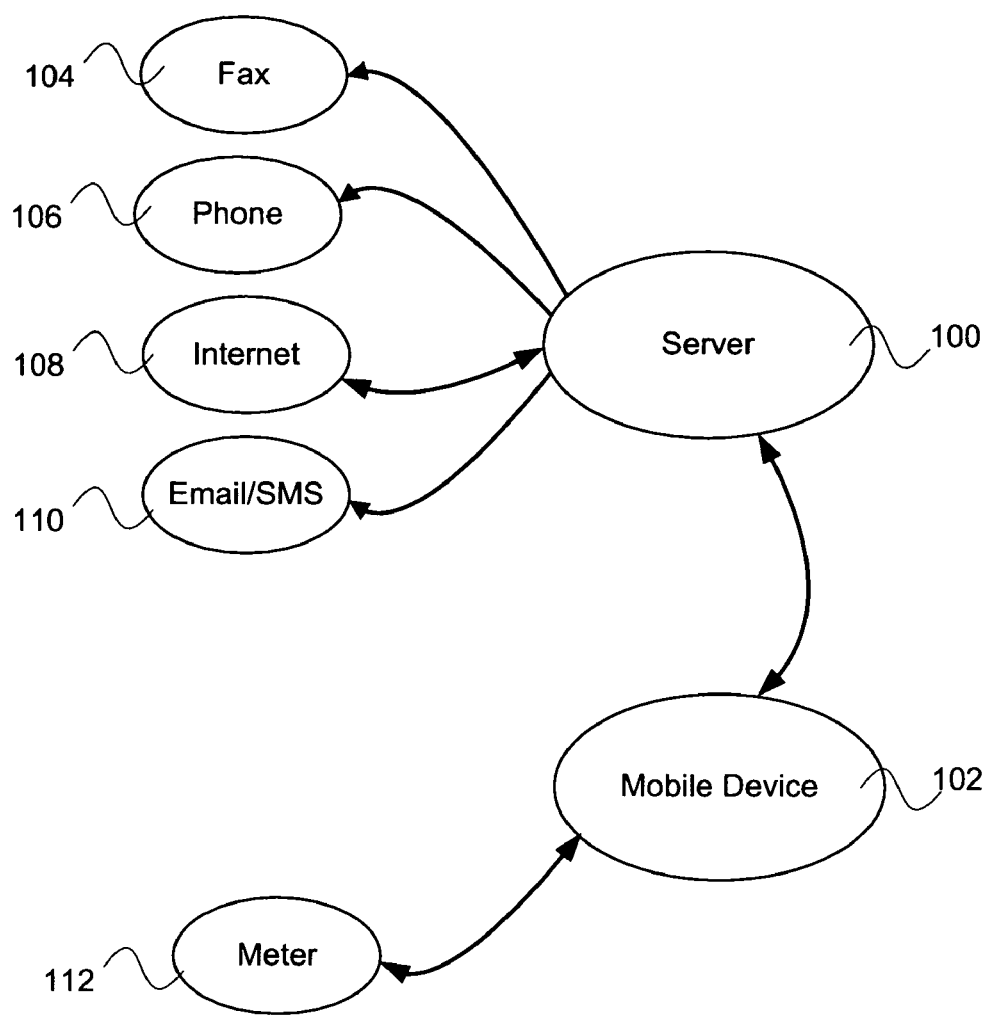
FIG. 1 illustrates an embodiment of a time-dependent health information system.

FIG. 1 illustrates an embodiment of a time-dependent health information system. In the example shown, server 100 and mobile device 102 communicate with one another. In some embodiments, the communication between server 100 and the mobile device 102 use the internet and cellular telephone networks. Server 100 is capable of communicating with fax 104, phone 106, and Email/SMS 110. In some embodiments, server 100 uses fax 104 to deliver a message to a health care practice team, medical research study team, a support team, a buddy, a family member, a health information system user, and/or a patient. A health care practice team includes, but is not limited to, a physician, a clinical nurse specialist, a nurse practitioner, a medical assistant, and/or a nutritionist. In some embodiments, server 100 uses phone 106 to deliver a message to a health care practice team, medical research study team, a support team, a buddy, a family member, and/or a patient. In some embodiments, server 100 uses Email/SMS 110 to deliver a message to a health care practice team, a support team, a buddy, a family member, and/or a patient. Server 100 is coupled to Internet 108. In some embodiments, server 100 communicates with a health care practice team or a medical research study team the status of a patient. Status includes displays of health information. In some embodiments, a health care practice team or a medical research study team communicates with server 100 information which is to be sent to a patient. In some embodiments, time dependent-health information is medical research study information. Medical research studies include clinical trials, clinical studies, observational studies, and epidemiological studies. In some embodiments, time dependent-health information is chronic illness information. Chronic illnesses include, but are not limited to, cardiovascular disease, chronic kidney disease, diabetes, asthma, chronic pain, depression, and obesity.

Mobile device 102 receives information from meter 112. In some embodiments, a health information system user enters information from meter 112 into mobile device 102. In some embodiments, meter 112 communicates with mobile device 102 electronically using a cable connection. In some embodiments, meter 112 communicates with mobile device 102 wirelessly. In some embodiments, mobile device 102 communicates information requests to meter 112. In some embodiments, the mobile device is a mobile phone. In some embodiments, the mobile device is a wirelessly connected personal data assistant (PDA).

Figure 2:
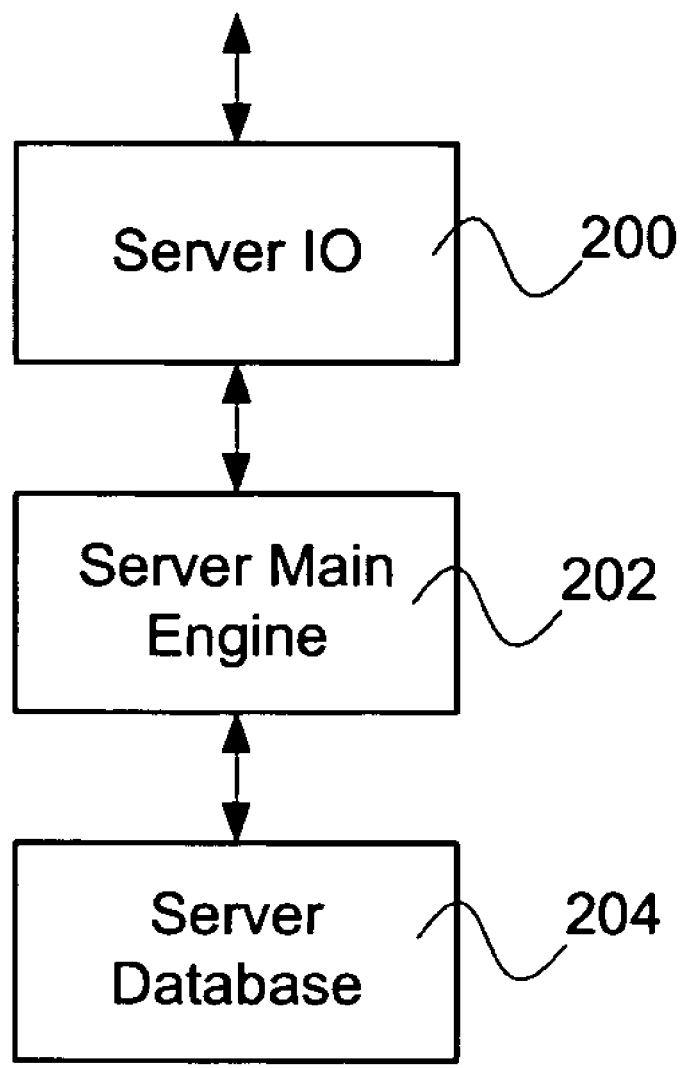
FIG. 2 illustrates an embodiment of a time-dependent health information system server.

FIG. 2 illustrates an embodiment of a time-dependent health information system server. In the example illustrated, server includes server IO 200, server main engine 202, and server database 204. Server IO 200 performs input and output functions for the server. In some embodiments, server IO 200 communicates with phones, faxes, emails, short message services, instant messaging services, the Internet/world wide web, and mobile devices. Server main engine 202 performs processing functions for the server including processing information in server database 204. In some embodiments, server main engine 202 processing includes calculating averages for health information, identifying out-of-norm or alarm conditions in health information, calculating degree of compliance, and creating summary information of health information. In some embodiments, server main engine 202 creates messages or reminders. Server database 204 performs data storage functions for the server. In some embodiments, server database 204 stores information including health meter readings, medication information, diet information, exercise information, and appointment information. In some embodiments, health meter readings include blood glucose readings, insulin readings, blood pressure readings, weight readings, HbA1c readings, urine readings, cholesterol readings, (LDL) readings, high-density lipoproteins (HDL) readings, and/or triglyceride readings. In some embodiments, health meter readings include peak flow readings. In some embodiments, medication information includes type of medication, time taken, and/or amount taken. In some embodiments, diet information includes calorie intake, fat intake, carbohydrate intake, and/or time of intake. In some embodiments, exercise information includes intensity information and/or duration information. In some embodiments, appointment information includes appointment times and locations with physicians and/or laboratories.

Figure 3:
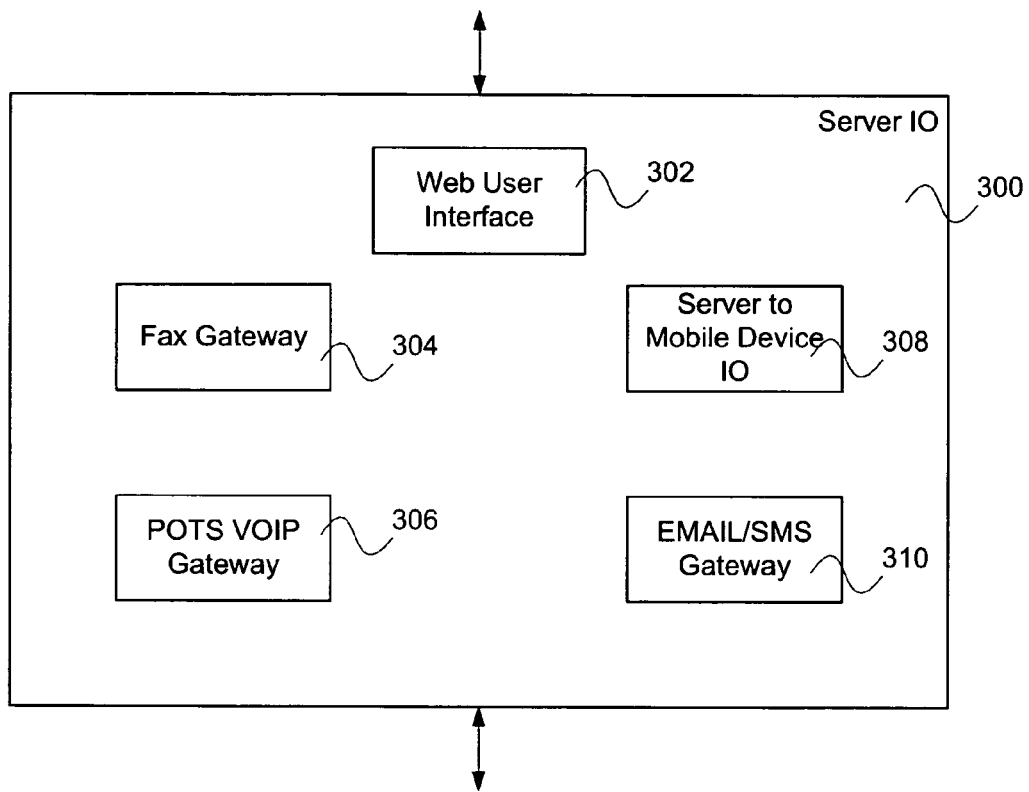
FIG. 3 illustrates an embodiment of server IO.

FIG. 3 illustrates an embodiment of server IO. Server IO 300 includes web user interface 302, fax gateway 304, plain old telephone service (POTS) voice over internet protocol (VOIP) gateway 306, server to mobile device IO 308, email/short message service (EMAIL/SMS) gateway 310. Web user interface 302 provides input and output interfaces for a user connected to the Internet/world wide web to communicate with the server. Fax gateway 304 provides an output interface for the server to deliver a message by fax. POTS VOW gateway 306 provides an output interface for the server to deliver a message by phone. Server to mobile device IO 308 provides input and output interfaces a mobile device to communicate with the server. EMAIL/SMS gateway 310 provides an output interface for the server to deliver a message by EMAIL and/or SMS.

Figure 4:
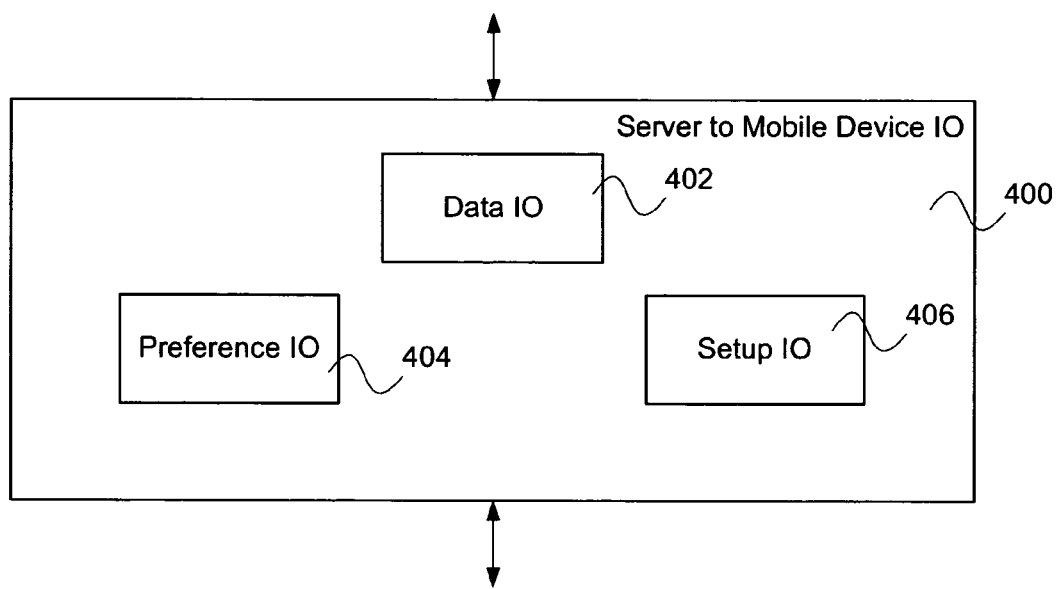
FIG. 4 illustrates an embodiment of server to mobile device IO.

FIG. 4 illustrates an embodiment of server to mobile device IO. Server to mobile device IO 400 includes data IO 402, preference IO 404, and setup IO 406. In some embodiments, data IO 402 includes input and output of health data information to be stored in health information database. In some embodiments, preference IO 404 includes input and output of user-specific information regarding daily schedule, glucose target levels, peak flow target levels, daily regimen reminders, personal information, out-of-norm or alarm trigger conditions, blood testing frequency, and/or medical appointments. In some embodiments, setup IO 406 includes user identification information and/or a password. In some embodiments, setup 10 includes mobile device information. In some embodiments, includes user identification information and/or a password. In some embodiments, setup IO includes billing information, category of chronic illness, and profile. Profile information includes testing regimens, measurement regimens, target levels, medication regimens, diet regimens, physical activity regimens, and/or appointment schedules. In some embodiments, setup IO information includes information for support team members, health care practice team, medical research study team members, physicians, buddies, and/or family members. In formation includes phone numbers, fax numbers, and/or email addresses.

Figure 5:
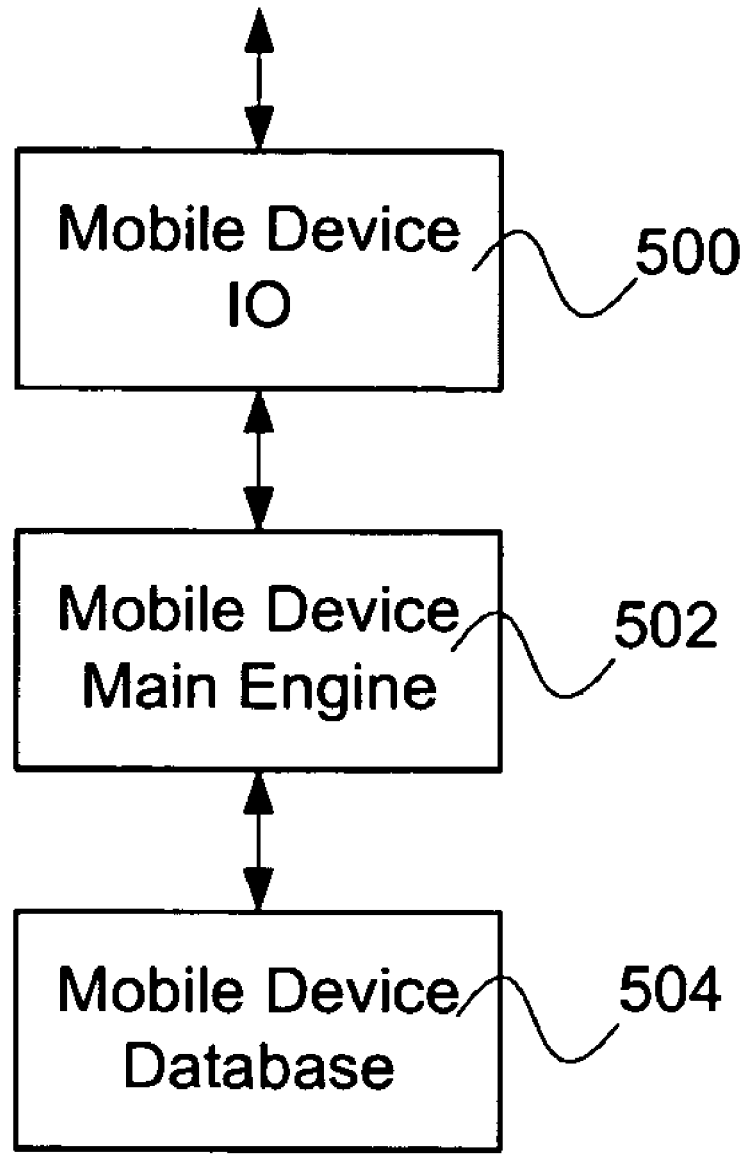
FIG. 5 illustrates an embodiment of a time-dependent health information system mobile device.

FIG. 5 illustrates an embodiment of a time-dependent health information system mobile device. In the example illustrated, mobile device includes mobile device IO 500, mobile device main engine 502, and mobile device database 504. Mobile device IO 500 performs input and output functions for the mobile device. In some embodiments, mobile device IO 500 communicates with devices, users, Internet/world wide web, and/or servers. In some embodiments, devices include health meters. In some embodiments, health meters include blood glucose meters, peak flow meters, weight measurement scales, and/or blood pressure meters. Mobile device main engine 502 performs processing functions for the mobile device including processing information in mobile device database 504. In some embodiments, mobile device main engine 502 processing includes calculating averages for health information, identifying out-of-norm or alarm conditions in health information, calculating degree of compliance, and creating summary information of health information. In some embodiments, mobile device main engine 502 creates messages or reminders. Mobile device database 504 performs data storage functions for the mobile device. In some embodiments, mobile device database 504 stores information including health meter readings, medication information, diet information, exercise information, and appointment information. In some embodiments, health meter readings include blood glucose readings, insulin readings, blood pressure readings, weight readings, peak flow readings, HbA1c readings, urine readings, cholesterol readings, and/or triglyceride readings. In some embodiments, medication information includes type of medication, time taken, and/or amount taken. In some embodiments, diet information includes calorie intake, fat intake, carbohydrate intake, and/or time of intake. In some embodiments, exercise information includes intensity information and/or duration information. In some embodiments, appointment information includes appoint times and locations with physicians and/or laboratories.

Figure 6:
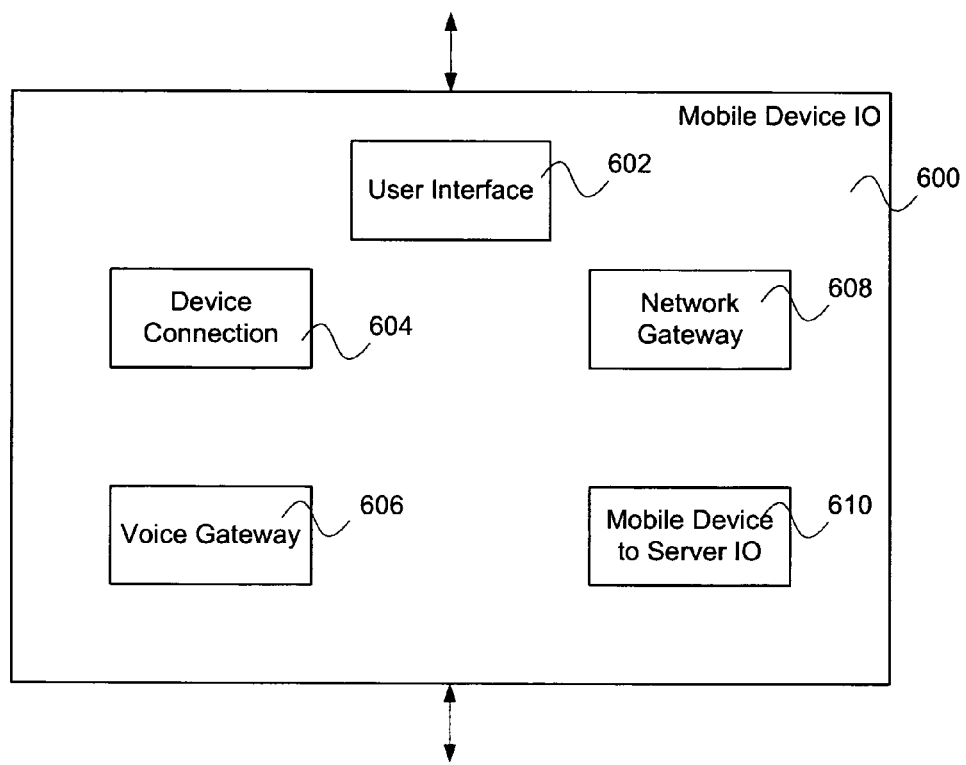
FIG. 6 illustrates an embodiment of mobile device IO.

FIG. 6 illustrates an embodiment of mobile device IO. Mobile device IO 600 includes user interface 602, device gateway 604, voice gateway 606, network gateway 608, and mobile device to server IO 610. Server to mobile device IO 610 includes data IO, preference IO, and setup IO. In some embodiments, data IO includes input and output of health data information to be stored in health information database. In some embodiments, preference IO includes input and output of user-specific information regarding daily schedule, glucose target levels, peak flow target levels, daily regimen reminders, personal information, out-of-norm or alarm trigger conditions, blood testing frequency, and/or medical appointments. In some embodiments, setup IO includes mobile device information. In some embodiments, includes user identification information and/or a password. In some embodiments, setup IO includes billing information, category of chronic illness, and profile. Profile information includes testing regimens, measurement regimens, medication regimens, diet regimens, physical activity regimens, and/or appointment schedules.

Figure 7:
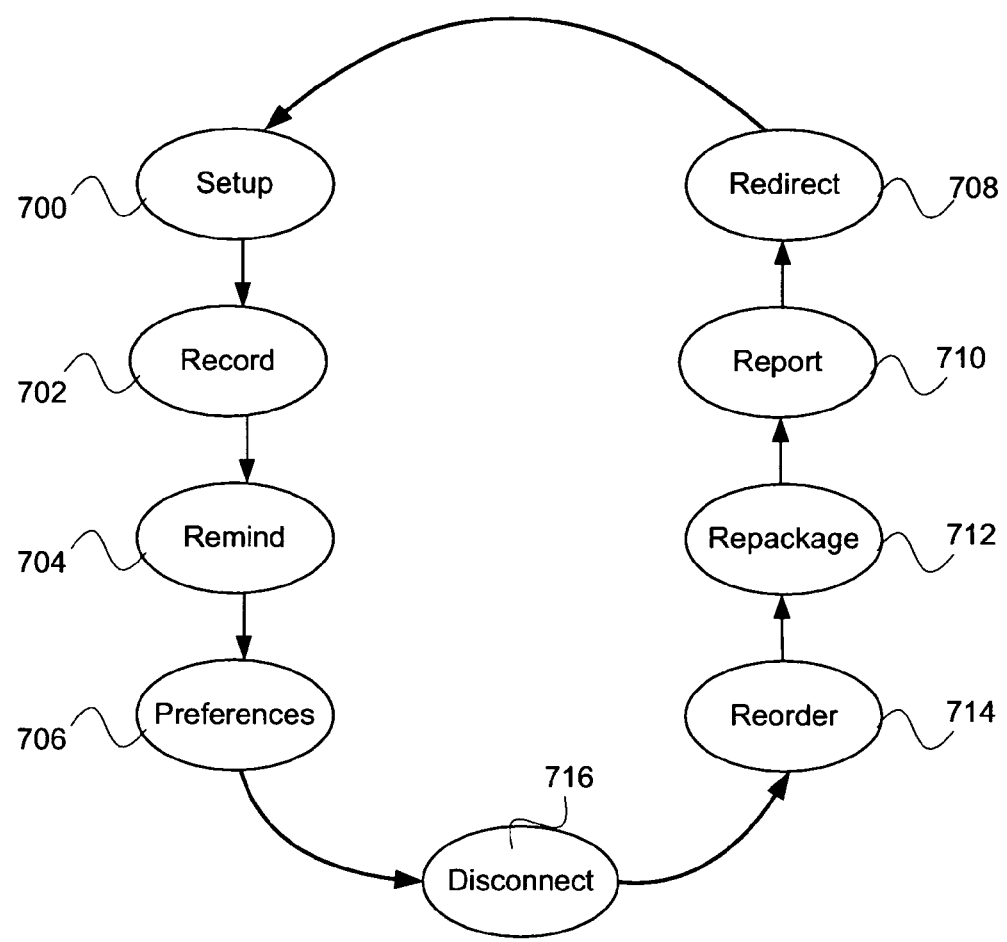
FIG. 7 illustrates an embodiment of health information system function blocks.

FIG. 7 illustrates an embodiment of health information system function blocks. Function blocks include setup 700, record 702, remind 704, preferences 706, redirect 708, report 710, repackage 712, reorder 714, and disconnect 716. Function blocks setup 700, record 702, preferences 706, report 710 and disconnect 716 are triggered by the user of the mobile device through the main menu of the application running on the mobile device. Function blocks remind 704, redirect 708, repackage 712, and reorder 714 are triggered by the system. In some embodiments, the main menu is a graphical user interface on the mobile device.

Setup 700 sets up a user to use the system. In some embodiments, setup 700 includes registering a user on the system, collecting preference information, creating appropriate application for the user's mobile device, and downloading the application to the mobile device. Record 702 records health information in the system. In some embodiments, record 702 includes entering the health information into the mobile device, time stamping the health information, storing the health information on the mobile device, giving the user feedback such as an instant report, uploading the health information to the server if a connection is possible, and queuing the upload for a later time if it is not possible to upload at this time. Remind 704 sends a reminder to a user. In some embodiments, remind 704 includes having a database indicate a reminder is required, deciding when to send the reminder based on user's previous on-time performance and on recent contact with user, and sending the reminder based on the user's reminder preference stated method.

Preferences 706 enters user-specific preferences into the system. In some embodiments, preferences 706 includes selecting preferences, connecting to server from mobile device, and uploading preferences to server. Redirect 708 sends information to someone other than the user. In some embodiments, redirect 708 includes checking for out-of-norm conditions, alarm conditions, a lack of recent and/or expected data from a patient. Redirect 708 also includes establishing the appropriate priority for the redirected message, sending the redirected message to the selected person or people using the preferred redirected method. Report 710 reports information stored in the health system database. In some embodiments, report 710 includes summarizing health information in a compact form for a user to review. Report 710 reports are viewed in graphical form or numerical form. Reports cover different time periods including the last 24 hours, the last 3 days, the last week, the last month, the last quarter.

Repackage 712 repackages information stored in the health system database. In some embodiments, repackage 712 includes summarizing health information in a compact form for physicians to review and sending the summary to the physician using a preferred method. Repackage 712 repackaged information is viewed in graphical form or numerical form. Repackaged information covers different time periods including the last 24 hours, the last 3 days, the last week, the last month, the last quarter. Reorder 714 reorders supplies and/or medication for the user. In some embodiments, reorder 714 includes determining that user supplies and/or medication are running low and ordering the supplies and/or medication from a preferred source in a timely manner so that the user will not run out of the supplies and/or medication. Disconnect 716 disconnects a user from the health information system. In some embodiments, disconnect 716 includes removing the patient data to a non-active user database, removal of the rules that were applied to a patient (including reminders and redirects), and removal of the patient preferences and data on the mobile phone.

Figure 8:
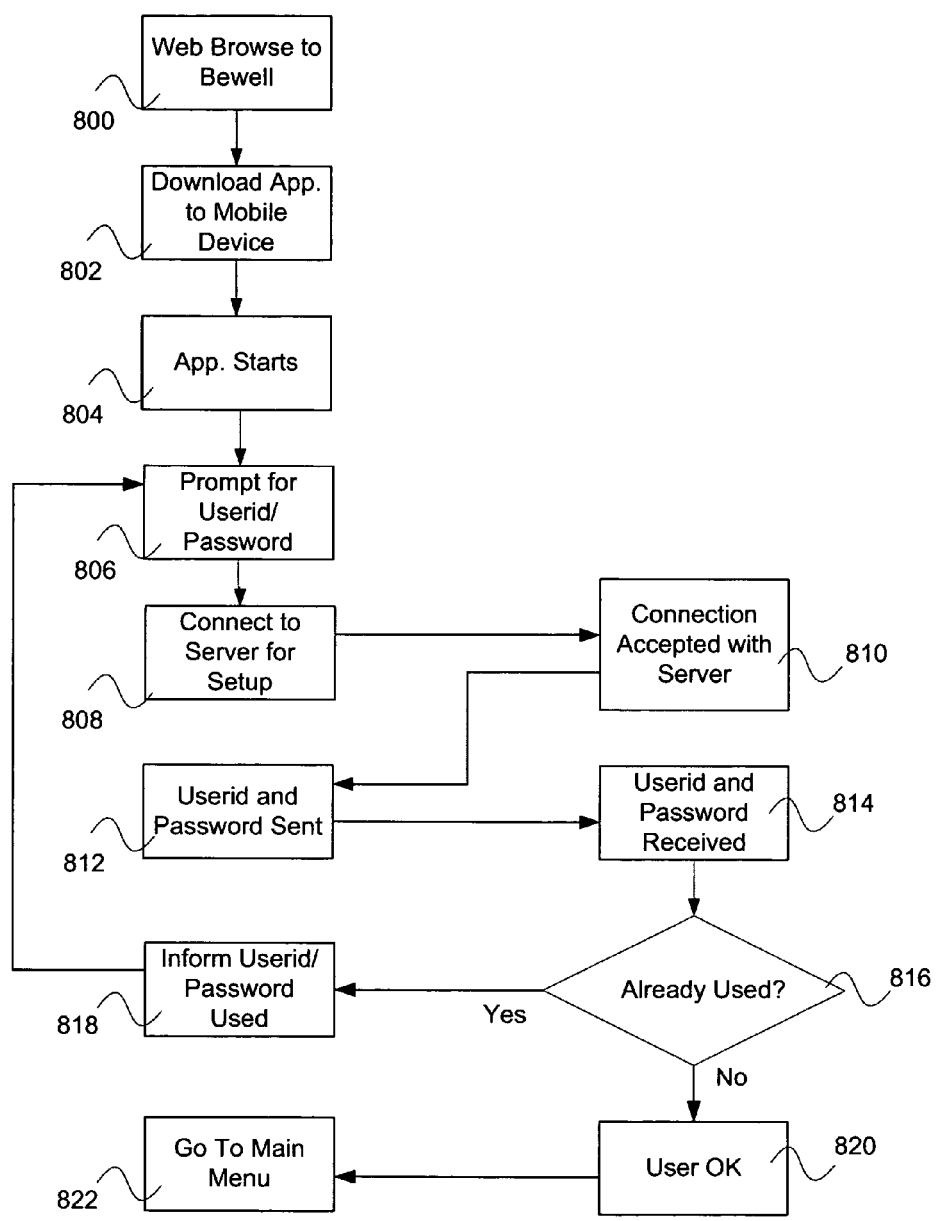
FIG. 8 illustrates an embodiment of a process for setup from the mobile device.

FIG. 8 illustrates an embodiment of a process for setup from the mobile device. In 800, a user uses a mobile device to web browse to the health information service system website. The health information service system website is the website related to the time-dependent health information system. In 802, the mobile device receives a download of an application that runs on the mobile device. In 804, the application starts running on the mobile device. In 806, the user is prompted for a user identification and a password. In 808, a connection is initiated from the mobile device to the server for setup. In 810, the connection is accepted by the server. In some embodiments, the server connection is with a header that provides for a secure connection. In 812, the user identification and password are sent from the mobile device to the server. In 814, the server receives the user identification and password. In 816, the user identification and password are checked against the existing database to see if the user identification and password are already used. If the user identification and password are used then the user is informed in 818, and the user is prompted for another user identification and password in 806. If the user identification and password is not used, then the user is established as OK in 820. In 822, the user is presented with the main menu of the application running on the mobile device.

Figure 9:
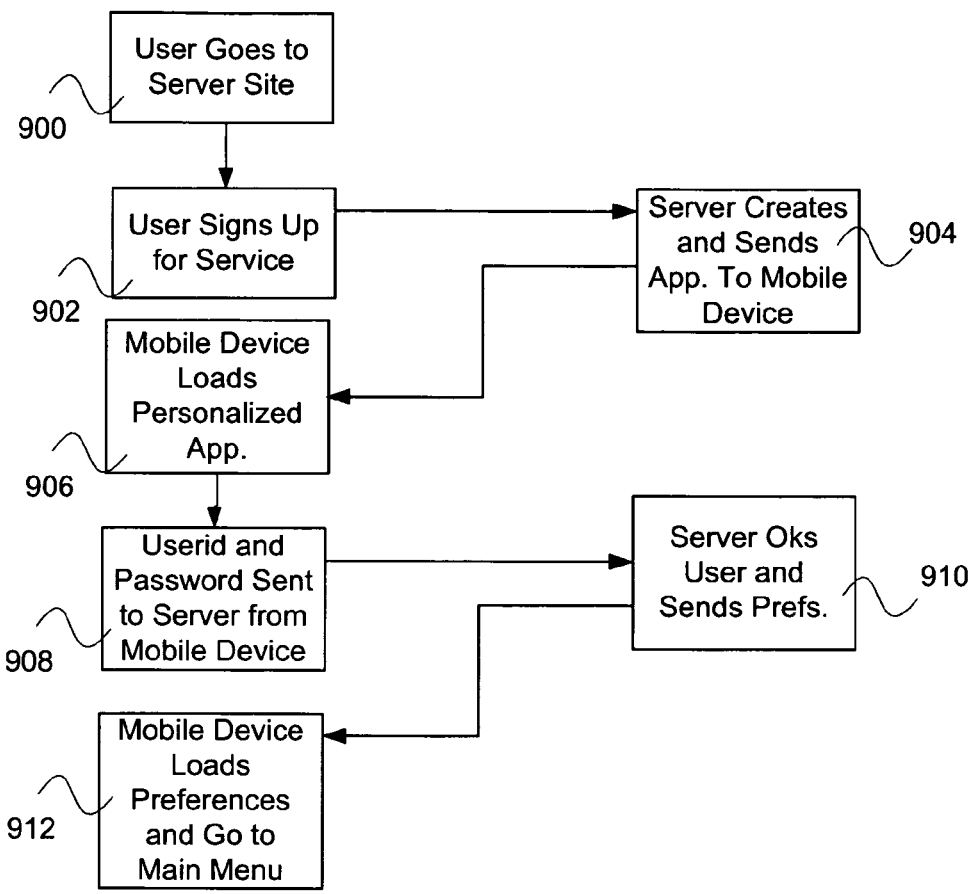
FIG. 9 illustrates an embodiment of a process for setup from the Internet/world wide web.

FIG. 9 illustrates an embodiment of a process for setup from the Internet/world wide web. In 900, a user uses a web browser to the health information service system website. The health information service system website is the website related to the time-dependent health information system. In 902, the user signs up for the health information service. In some embodiments, signing up includes providing user identification information, password, and/or user preferences. In some embodiments, preferences include user-specific information regarding daily schedule, glucose target levels, peak flow target levels, daily regimen reminders, personal information, out-of-norm or alarm trigger conditions, blood testing frequency, and/or medical appointments. In 904, server creates and sends personalized application to user's mobile device. In 906, mobile device receives, loads, and runs personalized application. In 908, user identification and password are sent to the server from the mobile device. In 910, server establishes that user is OK and sends preferences to mobile device. In 912, mobile device loads preferences and user is presented with the main menu of the application running on the mobile device.

Figure 10:
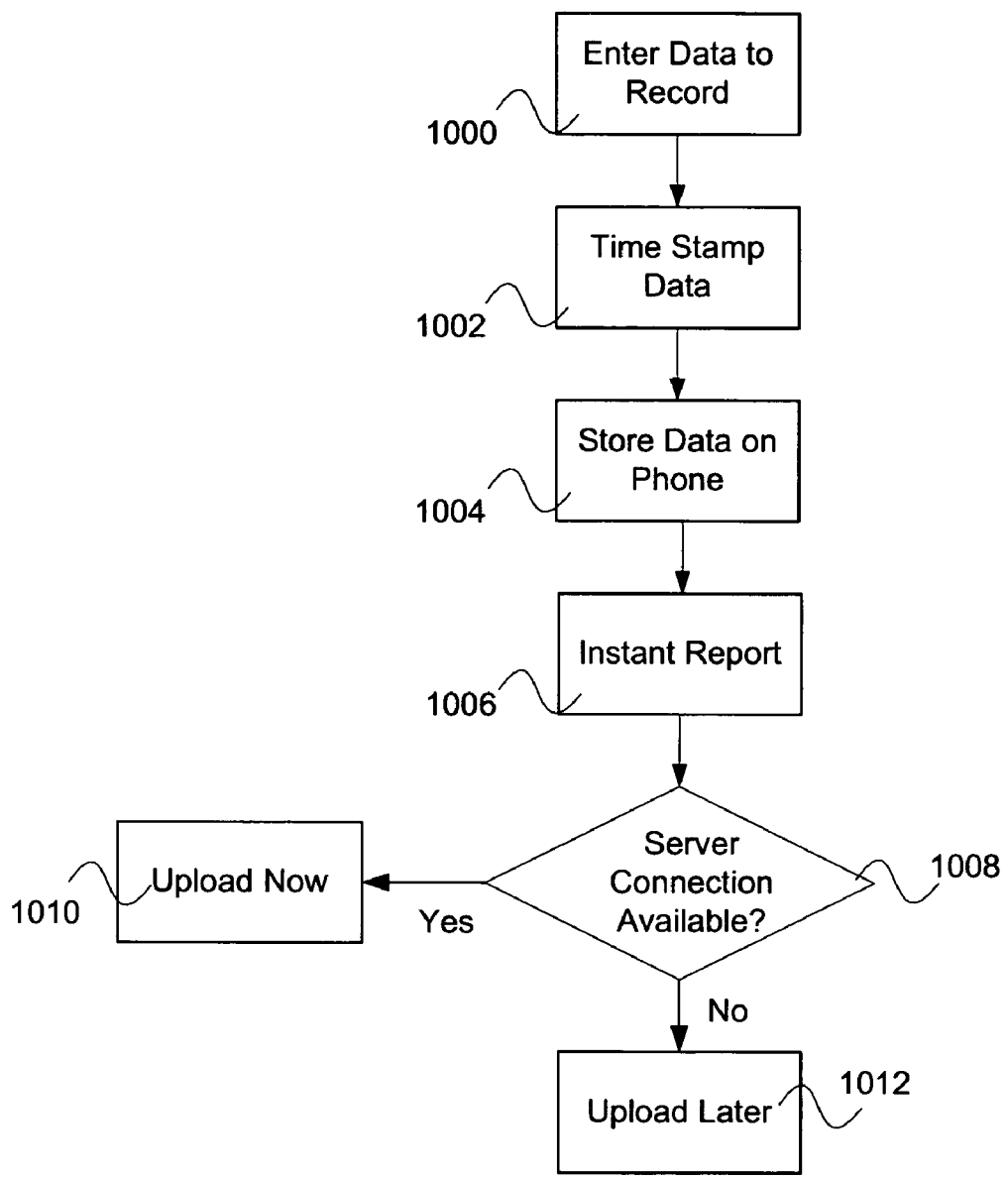
FIG. 10 illustrates an embodiment of a process for record.

FIG. 10 illustrates an embodiment of a process for record. In 1000, data is entered into the mobile device for recording. In some embodiments, the entering of data into the mobile device is achieved by manually inputting the data into the mobile device. In some embodiments, the inputting is using a keypad. In some embodiments, the inputting is using a pen based input system. In some embodiments, the inputting is using voice. In some embodiments, the entering of data into the mobile device is achieved electronically through a connection with a health monitoring device or meter. In some embodiments, the connection is a cable. In some embodiments, the entering of data into the mobile device is achieved wirelessly with a health monitoring device or meter. In some embodiments, the wireless entering of data uses infrared communication. In some embodiments, wireless entering of data uses Bluetooth® communication. In some embodiments, wireless entering of data uses 802.11 or Wi-Fi® type connection. In some embodiments, the user selects the type of meter that will enter data to the mobile device. In some embodiments, the mobile device will automatically sense the meter that will enter data and load the appropriate application programming interface. In some embodiments, the entered data can not be edited. Tamper proof data is an important feature for medical research study applications.

In 1002, the entered data is time stamped. In some embodiments, the time stamp include the time and date entered into the mobile device. In some embodiments, the time stamp can not be edited; the time stamp data is made tamper proof by preventing editing, or "tampering," of the time stamp. Tamper proof data is an important feature for medical research study applications. In 1004, the data is stored on the mobile device. In some embodiments, the data is stored on the mobile device so that storage space is conserved. In some embodiments, the data is maintained on the mobile device by storing the data in a progressively more compressed format the older the data is; recent data is stored at a fine granularity and older data at a coarse granularity. For example, each individual data point is stored for data entered today; average data for each day is stored for data entered in the last week; average data for each week is stored for data entered in the last month; and, average data for each month is stored for data entered in the last year.

In some embodiments, after the data is stored on the mobile device, the system response changes based on the user data. For example, the user profile is examined to determine if the user data indicates a green, yellow, or red zone condition. The green zone condition indicates that the user should follow the green zone action plan. The yellow zone condition indicates that the user should follow the yellow zone (caution zone) action plan. The red zone indicates that the user should follow the red zone (medical alert) action plan. In some embodiments, the green, yellow, and red plans are related to the health condition asthma. In some embodiments, after the data is stored on the mobile device, the user profile is examined to determined target ranges and/or similar time of day results for the past week's entries. In some embodiments, the ranges are blood glucose target ranges for a diabetic. In some embodiments, the similar time of day results are the after dinner results for the past week.

In 1006, an instant report is generated to provide feedback to the user. The mobile device is capable of calculation for instant reports and storage of data for the instant reports, so the mobile device is able to provide user functionality without a connection to the server or network. In some embodiments, the instant report is a graph showing the just entered health information along with health information previously entered. In some embodiments, the graph is a bar graph. In some embodiments, the graph is a pie chart. In some embodiments, the instant report is a display of numbers. In some embodiments, the numbers include averages and/or target ranges. In some embodiments, an instant report is not provided to the user. Having no instant report or user feedback is important for medical research study applications.

In 1008, it is determined if a server connection is available. If the server connection is available, data is uploaded now in 1010. If the server connection is not available, data is queued for uploading later in 1012. The mobile device is capable of storage of data which can be later uploaded to the server, so the mobile device is able to provide the user functionality without a connection to the server. In some embodiments, data uploaded includes data input to the mobile device, the time stamp information, and the user identification information.

In some embodiments, a point value is generated when a data value is stored. The point value is uploaded when the data value is uploaded. The point values are evaluated by the server to determine if a reward is due to the user. In some embodiments, the system generates a random point value when a data value is stored. In some embodiments, the point values are totaled and compared between users to determine if a reward is due to the user. In some embodiments, the reward is a download. In some embodiments, the download is a ring tone or a game.

Figure 11:
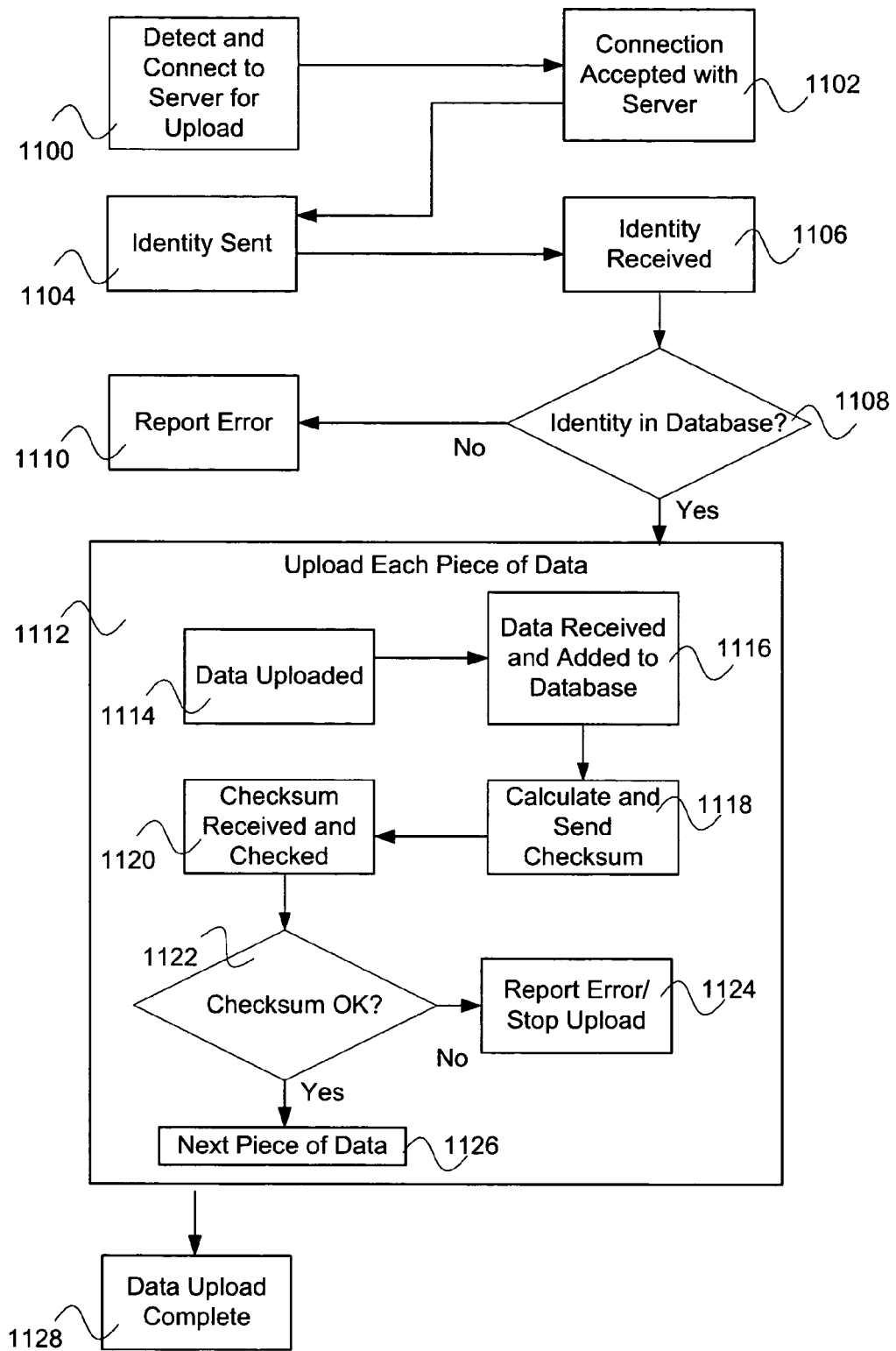
FIG. 11 illustrates an embodiment of a process for uploading.

FIG. 11 illustrates an embodiment of a process for uploading. In 1100, mobile device detects the availability of connecting to the server and connects to server for uploading. In 1102, the connection is accepted by the server. In some embodiments, the server connection is with a header that provides for a secure connection. In 1104, the mobile device sends identifying information to the server. In 1106, the server receives the identifying information. In 1108, it is determined if the identity is in the system database. If the identity is not in the system database, then an error is reported in 1110. If the identity is in the system database, then data is uploaded in 1112. For each piece of data to be uploaded, in 1114 data is uploaded from the mobile device to the server. In 1116, data is received and added to the database. In 1118, a checksum is calculated and sent from the server to the mobile device. In 1120, the checksum is received and checked. In 1122 if the checksum is not correct, an error is reported and the upload is stopped in 1124. If the checksum is correct, in 1126, the next piece of data is uploaded. If there is no more data, then the data upload is complete in 1128. In some embodiments, upload data is encrypted for security by the mobile device for uploading. In some embodiments, private/public key methods are used for encrypting the upload data.

Figure 12:
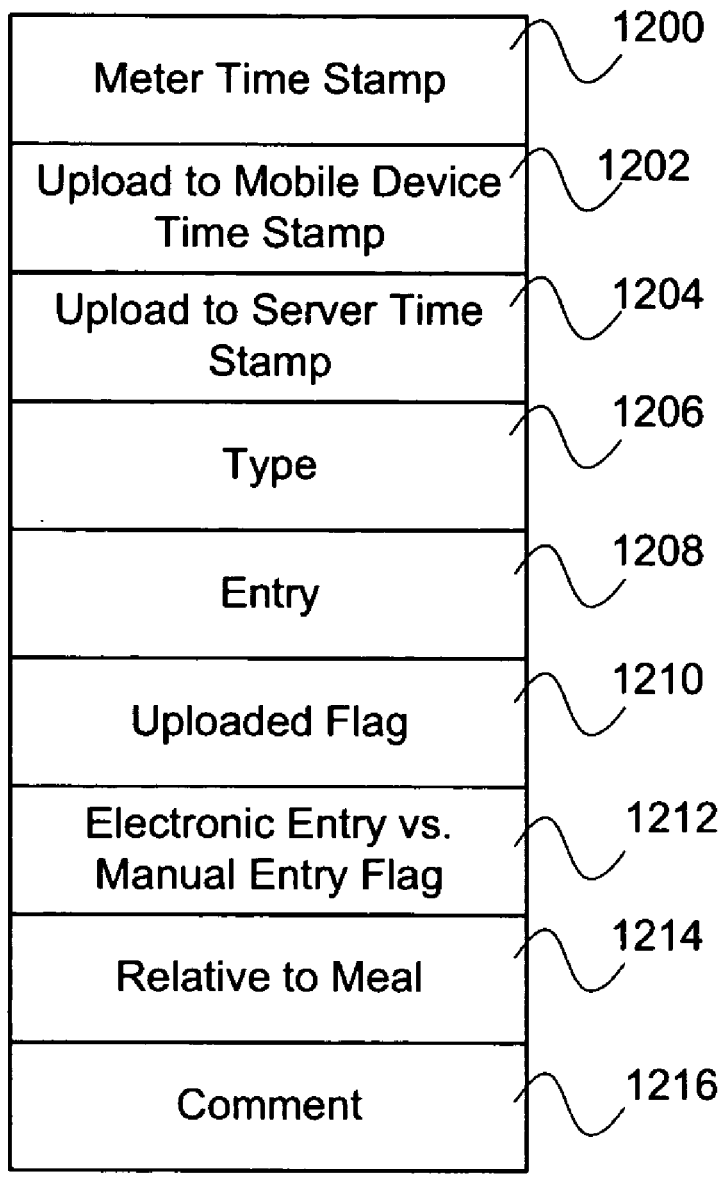
FIG. 12 illustrates an embodiment of a database data structure.

FIG. 12 illustrates an embodiment of a database data structure. Database data structure includes meter time stamp 1200, uploaded to mobile device time stamp 1202, uploaded to server time stamp 1204, type 1206, entry 1208, uploaded flag 1210, electronic entry vs. manual entry flag 1212, relative to meal 1214, and comment 1216. In some embodiments, meter time stamp 1200 indicates the time and date that the meter measured the value. In some embodiments, uploaded to mobile device time stamp 1202 indicates the time and date that the meter measured value was entered into the mobile device. In some embodiments, the uploaded to server time stamp 1204 indicates the time and date that the meter measured value was uploaded to the server. In some embodiments, type 1206 and entry 1208 are specific for diabetes. In some embodiments, type 1206 and entry 1208 are specific for asthma. In some embodiments, type 1206 include: exercise with entry 1208 as a duration in minutes and an intensity as a value where 1=low, 2=medium, and 3=high; glucose with entry 1208 as meter reading in milimoles per liter or units; insulin with entry 1208 as insulin units delivered; medication with entry 1208 as yes or no; blood pressure with entry 1208 as systolic value and diastolic value; carbohydrates with entry 1208 as a value in grams; weight with entry 1208 as a value in pounds; stress with entry 1208 as a value between 1 and 10; pain with entry 1208 as a value between 1 and 10; and HbA1c with entry as a hemoglobin value. In some embodiments, the uploaded flag indicates whether or not the data has been uploaded to the server from the mobile device. In some embodiments, the electronic entry vs. manual entry flag 1212 indicates which form of entry the data was entered into the mobile device. In some embodiments, relative to meal 1214 indicates the time the measured data is relative to a meal. For example, before or after breakfast, before or after lunch, before or after dinner, or before bedtime. In some embodiments, comment 1216 is a comment entered by the user about the data measurement.

Figure 13:
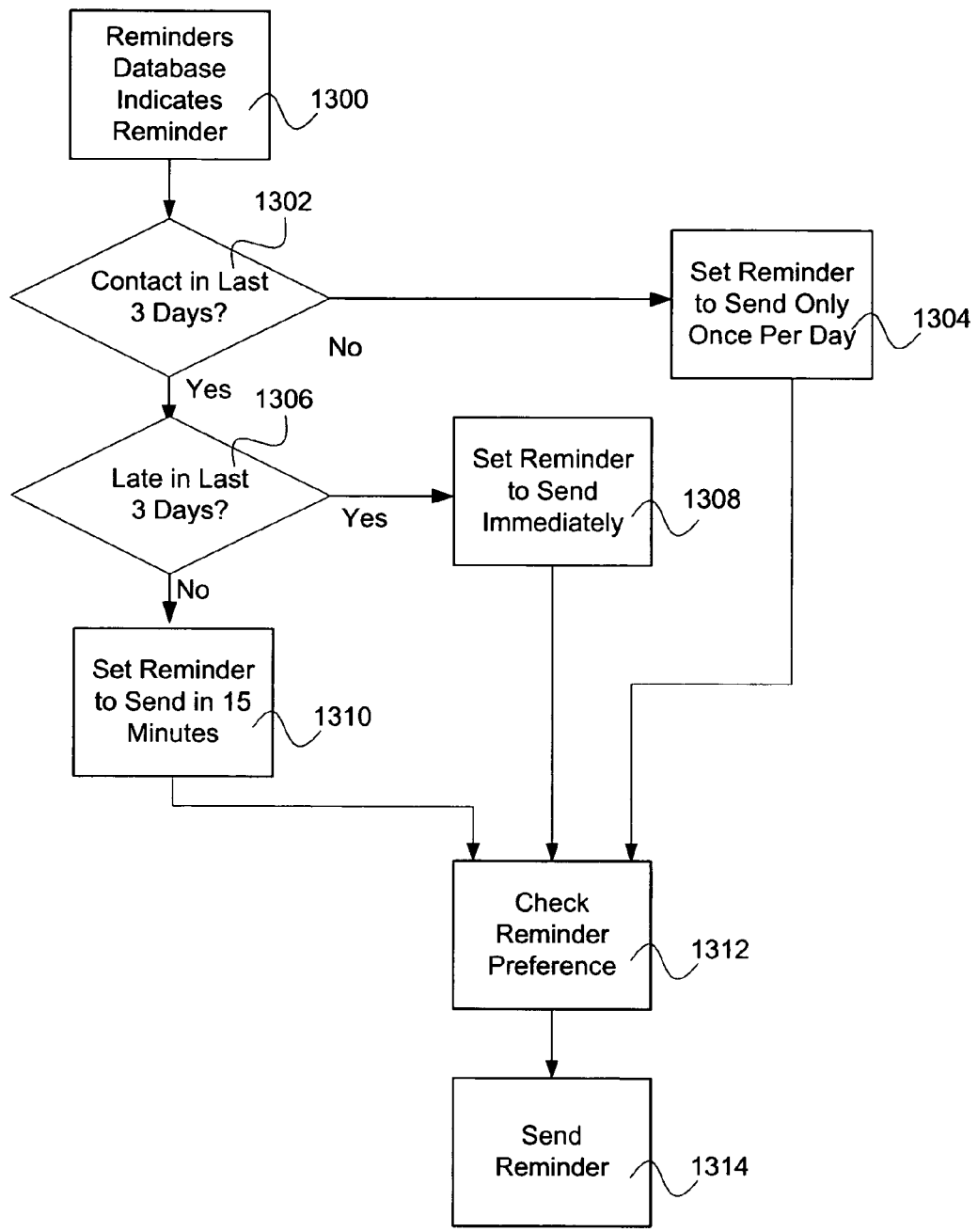
FIG. 13 illustrates an embodiment of a process for reminders.

FIG. 13 illustrates an embodiment of a process for reminders. In 1300, reminder database indicates that there is a reminder. In some embodiments, the reminder database contains a schedule of times that the user is to input health information into the system and when health information has been entered into the system. The reminder database indicates that there is a reminder if the user has not input health information by a scheduled time. In some embodiments, the reminder schedule is input to the system using the mobile device. In some embodiments, the reminder schedule is input to the system using the server. In 1302, it is determined if the user has interacted with the health information system within the last three days. If the user has not interacted within the last three days, then the user is generally not available to the system and the system then sends only one reminder per day in 1304. In some embodiments, the three day threshold is set to a different number of days. If the user has interacted within the last three days, then it is determined in 1306 if the user has entered data late in the last three days. If the user has been late within the last three days, then a reminder is sent immediately to the user in 1308. If the user has not been late within the last three days, then the reminder is queued in 1310 to be sent in 15 minutes. This queuing is to prevent reminder fatigue, the user may be only a little late and a reminder is not necessary unless the user is going to miss the measurement entirely. Whereas if the user is chronically late, a reminder is sent immediately to keep the user on schedule. In some embodiments, the 15 minute queued time delay is set to a different number of minutes. In 1312, the reminder preference is checked. In some embodiments, the preferred reminder method is set to be a fax message, a phone message, an EMAIL message, a SMS message, or an instant message. In 1314, a reminder is sent using the preferred method. In some embodiments, if a user does not upload health information after being reminded once, the user is reminded again.

Figure 14:
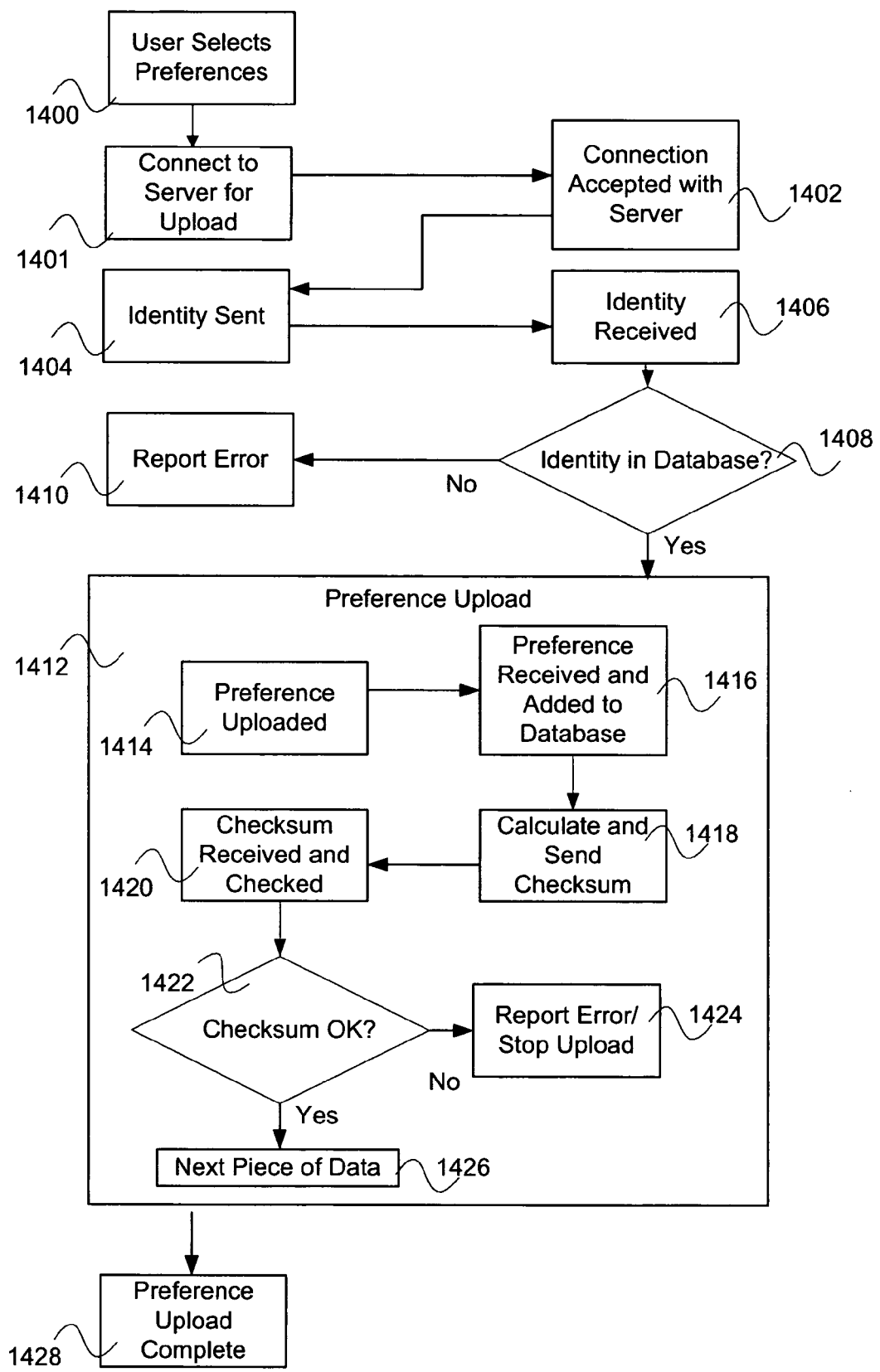
FIG. 14 illustrates an embodiment of a process for preference uploading.

FIG. 14 illustrates an embodiment of a process for preference uploading. In 1400, user selects preferences. In 1401, mobile device connects to server for uploading. In 1402, the connection is accepted by the server. In some embodiments, the server connection is with a header that provides for a secure connection. In 1404, the mobile device sends identifying information to the server. In 1406, the server receives the identifying information. In 1408, it is determined if the identity is in the system database. If the identity is not in the system database, then an error is reported in 1410. If the identity is in the system database, then preferences are uploaded in 1412. For each preference to be uploaded, in 1414 a preference is uploaded from the mobile device to the server. In 1416, the preference is received and added to the database. In 1418, a checksum is calculated and sent from the server to the mobile device. In 1420, the checksum is received and checked. In 1422 if the checksum is not correct, an error is reported and the upload is stopped in 1424. If the checksum is correct, in 1426, the next preference is uploaded. If there are no more preferences, then the preference upload is complete in 1428.

Figure 15:
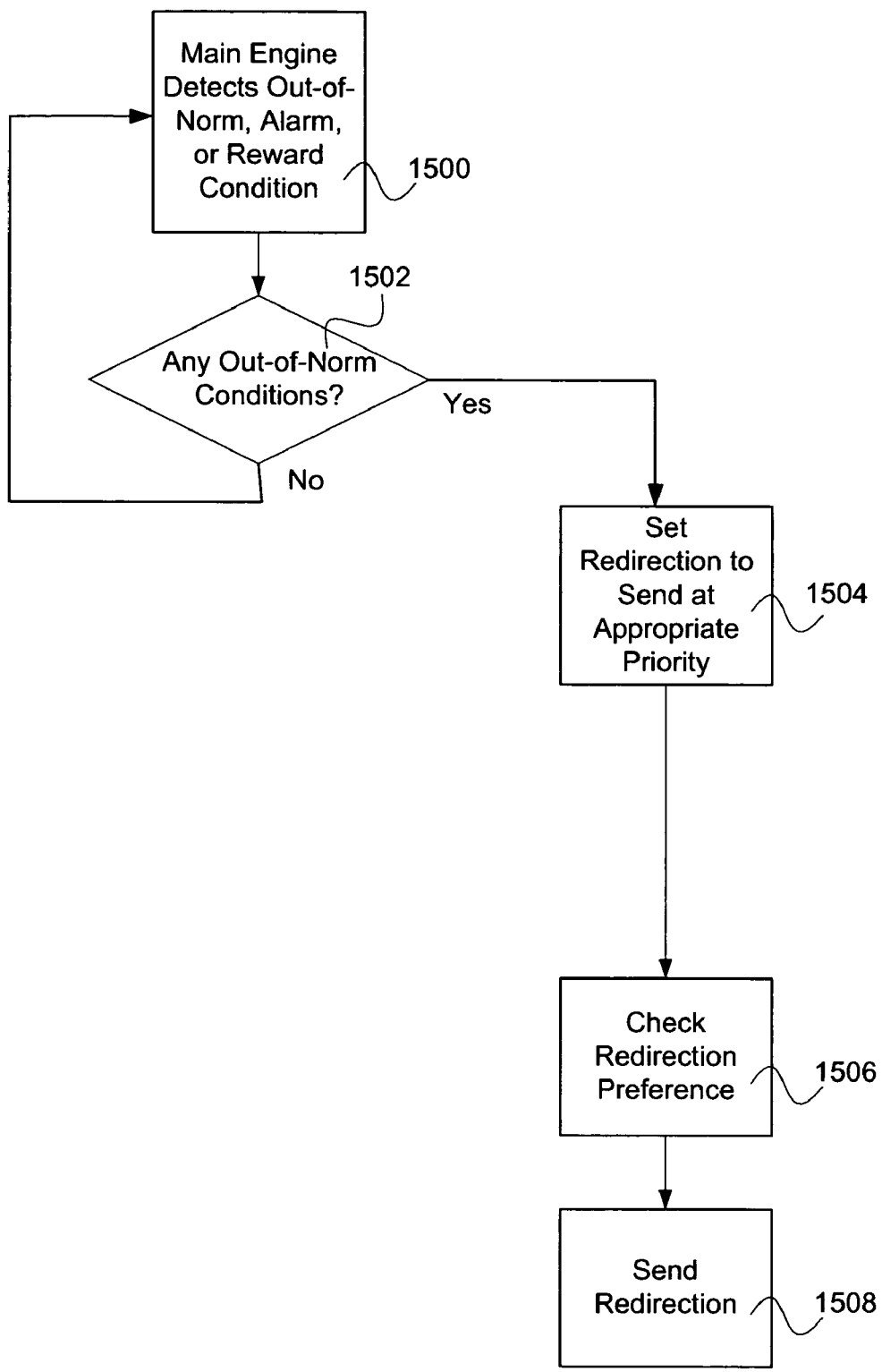
FIG. 15 illustrates an embodiment of a process for redirection.

FIG. 15 illustrates an embodiment of a process for redirection. In 1500, a main engine detects an out-of-norm, an alarm, or a reward condition. In some embodiments, the main engine is the server main engine. In some embodiments, an alarm condition is when with a given medical condition, certain thresholds are exceeded for a given type of measurement. For example, when for a patient with asthma, a peak flow reading is in the red zone or when for a patient with diabetes, a blood glucose reading is below the hypoglycemic threshold. In some embodiments, the main engine detects out-of-norm conditions by comparing input health information with norm limits for the health information. In some embodiments, alarm condition is based on not achieving a degree of compliance. If the health information is not within the norm limits, then an out-of-norm condition is detected. In some embodiments, a medical research study monitoring team is informed if the medical research study procedure is not being followed. In some embodiments, a reward condition is detected. Reward conditions include high degree of compliance. In 1502, if there are no out-of-norm, alarm, or reward conditions, then the main engine continues to check for out-of norm or alarm conditions in 1500. If there are out-of-norm, alarm, or reward conditions, then a redirection message is created to be sent at the appropriate priority in 1504. In some cases, the out-of-norm, alarm, or reward condition is critical and the message is urgently sent. In some cases, the out-of-norm, alarm, or reward condition is not critical and the message is not urgently sent. In 1506, the redirection preference is checked. In some embodiments, the preferred redirection method is set to be a fax message, a phone message, an EMAIL message, a SMS message, or an instant message. In some embodiments, the preferred redirection is a reward download. A reward download is a ring tone or game downloaded into the mobile device. In 1508, the redirection message is sent to the preferred redirection person using the preferred redirection method. In some embodiments, the preferred person is a physician, a support team member, a buddy, a family member, a health care practice team member, or a member of a clinical team. In some embodiments, the preferred person is a health system user. In some embodiments, the preferred person is multiple people. For example, a team can be rewarded if the team compliance achieves a certain level or has the best performance in a competition.

Figure 16:
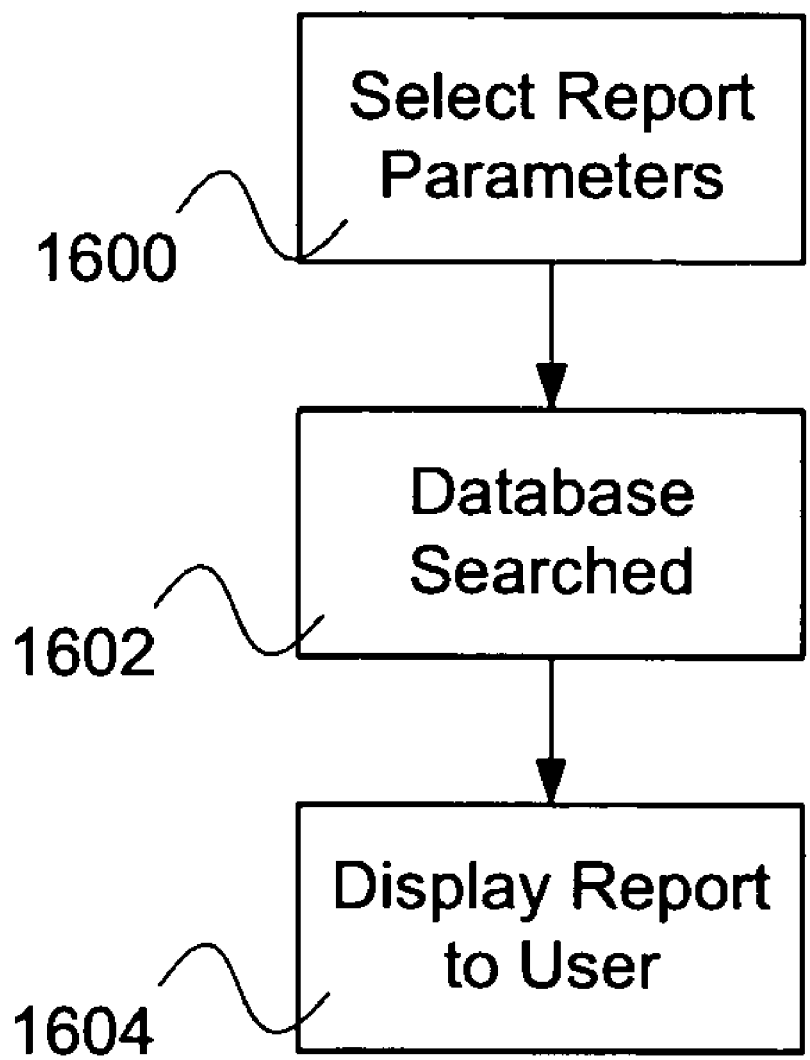
FIG. 16 illustrates an embodiment of a process for report.

FIG. 16 illustrates an embodiment of a process for report. In 1600, report parameters are selected by the user. In some embodiments, the parameters include condition, report type, time frame, and time of day. For diabetes, condition includes glucose reading, insulin intake, medication, blood pressure, weight, carbohydrates, stress, and exercise. For asthma, condition includes peak flow reading, control medication, rescue medication, nasal congestion, wheezing, coughing, shortness of breath, and level of activity. Report type includes bar chart, trend chart, pie chart, and text report. Time frame includes last 24 hours, last 2 days, last 4 days, last week, last 2 weeks, last month, and ever. For diabetes, time of day includes before breakfast, after breakfast, before lunch, after lunch, before dinner, after dinner, and bed time. For asthma, time of day includes wake up time, midday, and bed time. In 1602, the database is searched for the appropriate data for the report. In some embodiments, the database is the database on the mobile device. In some embodiments, the application on the mobile device searches the database on the mobile device. In 1604, the report is displayed to the user. In some embodiments, the report is displayed by the application on the mobile device.

Figure 17:
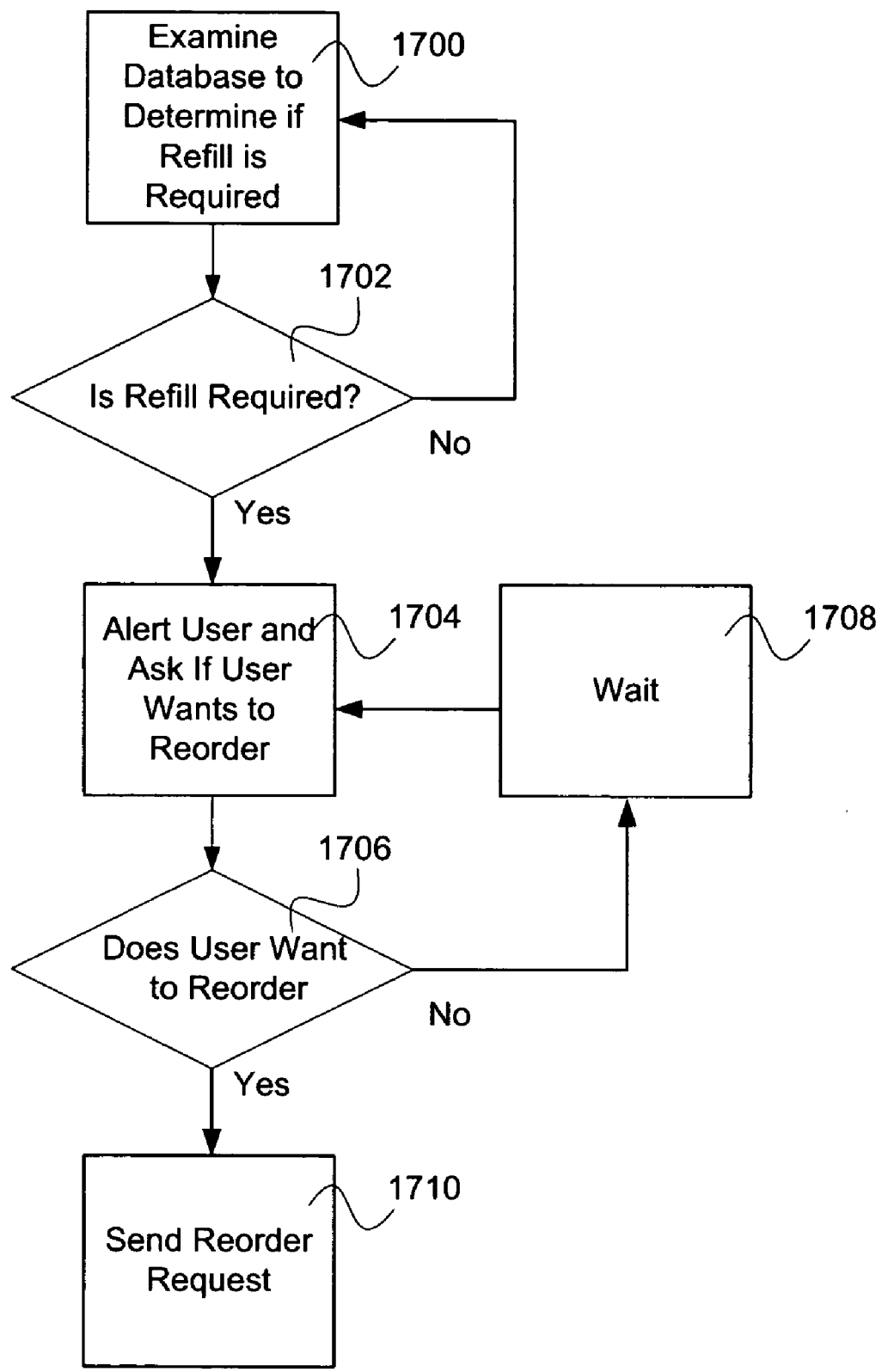
FIG. 17 illustrates an embodiment of a process for reorder.

FIG. 17 illustrates an embodiment of a process for reorder. In 1700, the database is examined to determine if refill is required. In some embodiments, patient medication profile information, medication usage information, medication next refill date information are used to determine if refill is required. In 1702, if refill is not required, database is examined to determine if refill is required in 1700. If refill is required, then in 1704 user is alerted and asked if user wants a reorder. In 1706, if user does not want a reorder then in 1708 the system waits before the user is alerted again and asked if user wants a reorder in 1704. If user does want a reorder, then in 1710 a reorder request is sent. In some embodiments, the reorder request is sent to a pharmacy. In some embodiments, the request is sent electronically. In some embodiments, the request is acknowledged by the pharmacy.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of acquiring and managing time dependent health information comprising:
   determining on the mobile device whether a time dependent health information has been received at a mobile device according to a schedule;
   in the event that the time dependent health information has not been received according to the schedule,
      determining on the mobile device whether prior time dependent health information has also not been received at the mobile device according to the schedule;
   in the event that prior time dependent health information has also not been received according to the schedule, providing an immediate reminder to input the time dependent health information, wherein the immediate reminder is provided to the user using an interface on the mobile device;
   in the event that prior time dependent health information has been received according to the schedule, queuing a delayed reminder to input the time dependent health information, wherein the delayed reminder is provided to the user using the interface on the mobile device;
   in the event that the time dependent health information has been received according to schedule:
      time stamping the time dependent health information;
      storing the time stamped time dependent health information on the mobile device;
      maintaining the time stamped time dependent health information on the mobile device wherein maintaining comprises storing today's information at a finer granularity than information older than today's information, wherein a coarser granularity is achieved using averaging over one or more different time period lengths for information older than today;
      calculating and displaying a graph for a report on the mobile device using the time stamped time dependent health information;
      determining the availability of the connection to the server; and
      in the event that the connection to the server is available, uploading the time stamped time dependent health information and a user identifier to the server.

2. A method as recited in claim 1, wherein the time dependent health information is medical research study information.

3. A method as recited in claim 1, wherein the time dependent health information is chronic illness information.

4. A method as recited in claim 1, wherein the time dependent health information is chronic illness information wherein the chronic illness is diabetes information.

5. A method as recited in claim 1, wherein the time dependent health information is chronic illness information wherein the chronic illness is asthma information.

6. A method as recited in claim 1, further comprising changing the system response based on the stored time dependent health information.

7. A method as recited in claim 1, further comprising changing the system response based on the stored time dependent health information wherein the change in the system response is changing an action plan.

8. A method as recited in claim 1, wherein inputting the time dependent health information is manually input.

9. A method as recited in claim 1, wherein inputting the time dependent health information is manually input using a keypad.

10. A method as recited in claim 1, wherein inputting the time dependent health information is input using voice.

11. A method as recited in claim 1, wherein inputting the time dependent health information is electronically input.

12. A method as recited in claim 1, wherein inputting the time dependent health information is electronically input using a cable connection.

13. A method as recited in claim 1, wherein inputting the time dependent health information is wirelessly input.

14. A method as recited in claim 1, further comprising selecting an input device.

15. A method as recited in claim 1, further comprising selecting an input device wherein selecting is manually selecting the input device.

16. A method as recited in claim 1, further comprising selecting an input device wherein selecting is having the mobile device detect and select an input device.

17. A method as recited in claim 1, further comprising reminding the user to enter time dependent health information in the event that the user has not entered the information by a scheduled time wherein the scheduled time is input using the mobile device.

18. A method as recited in claim 1, further comprising reminding the user to enter time dependent health information in the event that the user has not entered the information by a scheduled time wherein the scheduled time is input using the server.

19. A method as recited in claim 1, further comprising reminding the user to enter time dependent health information in the event that the user has not entered the information by a scheduled time wherein the reminding the user uses a preferred reminder method.

20. A method as recited in claim 1, further comprising detecting an alarm condition and sending a message to a preferred redirection person using a preferred redirection method.

21. A method as recited in claim 1, further comprising detecting a reward condition and sending a message to a preferred redirection person using a preferred redirection method.

22. A method as recited in claim 1, further comprising detecting a reward condition and sending a download to a preferred redirection person using a preferred redirection method.

23. A method as recited in claim 1, further comprising detecting an out-of-norm condition and sending a message to a preferred redirection person using a preferred redirection method.

24. A method as recited in claim 1, further comprising detecting an out-of-norm condition and sending a message to a preferred redirection person using a preferred redirection method wherein detecting out-of-norm conditions comprises determining if input time dependent health information exceeds a norm limit.

25. A system for acquiring and managing time dependent health information comprising:
  a mobile device comprises a processor, a storage facility, and an input/output module, wherein the processor is configured to:
  determine whether a time dependent health information has been received on a mobile device according to a schedule;
  providing provide an immediate reminder to input the time dependent health information in the event that prior time dependent health information has also not been received according to the schedule to the user using an input/output module on the mobile device;
  provide a delayed reminder to input the time dependent health information in the event that prior time dependent health information has been received according to the schedule to the user using an the input/output module on the mobile device; and stamp the time dependent health information; and
  wherein the storage facility stores on the mobile device the time stamped time dependent health information; and
  wherein the processor is further configured to: maintain the time stamped time dependent health information on the mobile device wherein maintaining comprises storing today's information at a finer granularity than information older than today's information, wherein a coarser granularity is achieved using averaging over one or more different time period lengths for information older than today; and
  calculate on the mobile device using the time stamped time dependent health information a graph for a report; and
  wherein the input/output module is configured to: a detector for detecting the graph for the report and determine the availability of the connection to the server; and
  in the event that the connection to the server is available, provide the uploaded time stamped time dependent health information and a user identifier to the server.

26. A method of acquiring and managing time dependent health information comprising:
  determining on the cell phone whether a time dependent health information has been received at a cell phone according to a schedule;
  in the event that the time dependent health information has not been received according to the schedule,
    determining on the cell phone whether prior time dependent health information has also not been received at the cell phone according to the schedule;
    in the event that prior time dependent health information has also not been received according to the schedule, providing an immediate reminder to input the time dependent health information, wherein the immediate reminder is provided to the user using an interface on the cell phone;
    in the event that prior time dependent health information has been received according to the schedule, queuing a delayed reminder to input the time dependent health information, wherein the delayed reminder is provided to the user using the interface on the cell phone;
  in the event that the time dependent health information has been received according to schedule:
    time stamping the time dependent health information, wherein the time stamping comprises storing a time stamp associated with the time dependent health information, wherein the stored time stamp is tamper proof;
    storing the time stamped time dependent health information on the cell phone;
    maintaining the time stamped time dependent health information on the cell phone wherein maintaining comprises storing today's information at a finer granularity than information older than today's information, wherein the finer granularity uses averaging over a shorter time, wherein a coarser granularity is achieved using averaging over one or more different time period lengths for information older than today;
    calculating on the cell phone using the time stamped time dependent health information a graph for a report without requiring a connection to a server;
    displaying on the cell phone the graph for the report;
    determining the availability of the connection to the server; and
    in the event that the connection to the server is available, uploading the time stamped time dependent health information and a user identifier to the server.

* * * * *